(12) United States Patent
Nashed (10) Patent No.: US 7,004,163 B2
(45) Date of Patent: Feb. 28, 2006

(54) GAS DELIVERY, EVACUATION AND RESPIRATORY MONITORING SYSTEM AND METHOD

(76) Inventor: Ramses Nashed, 505 First Ave. South, Tierra Verde, FL (US) 33715

( * ) Notice: Subject to any disclaimer, the term of this patent is extended or adjusted under 35 U.S.C. 154(b) by 0 days.

(21) Appl. No.: 10/747,638

(22) Filed: Dec. 29, 2003

(65) Prior Publication Data
US 2005/0145247 A1 Jul. 7, 2005

(51) Int. Cl.
*A62B 17/04* (2006.01)
*A62B 18/00* (2006.01)

(52) U.S. Cl. .................... 128/201.22; 128/203.18; 128/204.22

(58) Field of Classification Search ........... 128/201.22, 128/201.23, 201.25, 201.28, 203.12, 203.13, 128/203.14, 203.18, 204.18, 204.21, 204.22, 128/205.12, 205.23, 205.24, 205.25–205.29, 128/206.12, 206.15, 206.21, 206.24–206.28, 128/207.11–207.17, 910–914
See application file for complete search history.

(56) References Cited

U.S. PATENT DOCUMENTS

| | | | | |
|---|---|---|---|---|
| 2,222,971 A | * | 11/1940 | Wright | 128/201.15 |
| 4,989,596 A | * | 2/1991 | Macris et al. | 128/201.28 |
| 5,676,133 A | * | 10/1997 | Hickle et al. | 128/205.12 |

* cited by examiner

*Primary Examiner*—Henry Bennett
*Assistant Examiner*—D. Doster-Greene
(74) *Attorney, Agent, or Firm*—Edward P. Dutkiewicz (57) ABSTRACT

A carbon-dioxide sampling tube operatively couples a capnograph and an exhaust-gas sampling tube of a mask. The mask has an ambient-to-inside-the mask inflow flapper valve located on a wall of the mask, a fresh-gas inflow tube, an exhaust-gas outflow tube, and a gas sampling tube. A fresh gas inflow tube operatively couples a fresh gas source and the face mask. An exhaust-gas hose operatively couples a scavenging system and the exhaust gas outflow tube.

6 Claims, 5 Drawing Sheets

GAS DELIVERY, EVACUATION AND RESPIRATORY MONITORING SYSTEM AND METHOD

BACKGROUND OF THE INVENTION

1. Field of the Invention

The present invention relates to a gas delivery, evacuation and respiratory monitoring system and method and more particularly pertains to allowing a user to deliver at least one gas and scavenge the exhausted gasses as well as monitor the exhausted gasses in a safe and efficient manner.

2. Description of the Prior Art

The use of gas handling systems is known in the prior art. More specifically, gas handling systems previously devised and utilized for the purpose of delivering and/or evacuating and/or monitoring a gas flow are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 4,328,797 issued on May 11, 1982 and is related to a naso-gastric oxygen mask. In addition, U.S. Pat. No. 2,023,267 issued on Dec. 3, 1935 and is related to a feeding means for gas masks.

While these devices fulfill their respective, particular objectives and requirements, the aforementioned patents do not describe a gas delivery, evacuation and respiratory monitoring system and method that allows allowing a user to deliver at least one gas and scavenge the exhausted gasses as well as monitor the exhausted gasses in a safe and efficient manner.

In this respect, a gas delivery, evacuation and respiratory monitoring system and method according to the present invention substantially departs from the conventional concepts and designs of the prior art, and in doing so provides an apparatus primarily designed and developed for the purpose of allowing a user to deliver at least one gas and scavenge the exhausted gasses as well as monitor the exhausted gasses in a safe and efficient manner.

Therefore, it can be appreciated that there exists a continuing need for a new and improved a gas delivery, evacuation and respiratory monitoring system and associated method which can be used for allowing a user to deliver at least one gas and scavenge the exhausted gasses as well as to concurrently monitor the exhausted gasses in a both a safe and efficient manner. In this regard, the present invention substantially fulfills this need.

SUMMARY OF THE INVENTION

In view of the foregoing disadvantages inherent in the known types of gas handling systems now present in the prior art, the present invention provides an improved a gas delivery, evacuation and respiratory monitoring system and method. As such, the general purpose of the present invention, which will be described subsequently in greater detail, is to provide a new and improved a gas delivery, evacuation and respiratory monitoring system and method which has all the advantages of the prior art and none of the disadvantages.

To attain this, the present invention essentially comprises a gas delivery, evacuation and respiratory monitoring system is disclosed. The system allows a user to deliver at least one gas and scavenge the exhausted gasses. The system also allows a user to monitor the exhausted gases. The delivery, scavenging and monitoring can be done in a safe and efficient manner. The system comprises several components in combination.

First provided is a face mask. The face mask is fabricated of a flexible material. The face mask has a face recipient area and a continuous side wall area and a dome area. Te areas are continuous and form a surface. The mask has an upper portion and a lower portion. The dome area is located in the upper portion of the mask. The dome forms a closed, recessed portion of the mask. The face mask has a nasal portion of a first width and a mouth portion of a second width. The nasal and mouth portions are continuous, with the second width being larger than the first width. The mask has a continuous side-wall portion with the side-wall portion having at least one intake hole there through. The intake hole has an associated flapper valve, to permit the passage of a gas into the mask from the surrounding atmosphere and to prevent the gas from within the mask moving into the surrounding atmosphere.

The mask has a head strap that is coupled to the side wall of the mask to hold the mask in place. The dome area has a fresh-gas inflow tube of a first internal diameter coupled there to. The inflow tube has an inner portion and an outer portion. The inner portion is coupled to the dome area of the face mask. The outer portion of the fresh-gas inflow tube has a tapered external second diameter to allow the slip-fit there onto. The dome area also has an exhaust-gas outflow tube of a third internal diameter and a fourth external diameter. The fourth diameter is larger than the first and second and third diameters. The exhaust-gas outflow tube has an inner portion and an outer portion. The inner portion is coupled to the dome area of the face mask. The outer portion of the gas outflow tube is configured to allow the slip fit there onto. The gas outflow tube also has an exhaust-gas sampling tube of a fifth internal diameter coupled to the inner portion of the exhaust-gas outflow tube. The fifth diameter is smaller than the first, second, third and fourth diameters. The exhaust-gas sampling tube has an inward end coupled to the exhaust-gas outflow tube and an outward end. The outward end has a male coupling thread.

The component next provided is a fresh gas source having a outflow tube.

Next provided is a fresh gas supply tube fabricated of a flexible material. The gas supply tube has an inflow end and an outflow end having a second internal diameter. The inflow end is coupled to the outflow tube of the fresh gas source. The outflow end is coupled to the outer portion of the fresh-gas inflow tube of the face mask. Next provided is an exhaust-gas scavenging system having an inflow tube.

An exhaust-gas hose is next provided. The exhaust-gas hose is fabricated of flexible material and has an inflow end and an outflow end. The outflow end is coupled to the inflow tube of the exhaust-gas scavenging system. The inflow end has a fourth internal diameter so as to allow the exhaust-gas hose to be slipped onto and coupled with the outer portion of the exhaust-gas outflow tube.

Next provided is a carbon-dioxide monitoring device, also known as a capnograph. The device has a sample inflow tube for receiving gas samples.

Lastly provided is a carbon-dioxide sampling tube fabricated of a flexible material and having a fifth diameter. The carbon-dioxide sampling tube has an inflow end and an outflow end. The outflow end is operatively coupled to the capnograph sample inflow tube. The inflow end of the carbon-dioxide sampling tube has a female treaded coupler for receiving and coupling with the outward end of the exhaust-gas sampling tube of the mask.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved a gas delivery, evacuation and respiratory monitoring system and method which has all of the advantages of the prior art gas handling systems and none of the disadvantages.

It is another object of the present invention to provide a new and improved a gas delivery, evacuation and respiratory monitoring system and method which may be easily and efficiently manufactured and marketed.

It is further object of the present invention to provide a new and improved a gas delivery, evacuation and respiratory monitoring system and method which is of durable and reliable constructions.

An even further object of the present invention is to provide a new and improved a gas delivery, evacuation and respiratory monitoring system and method which is susceptible of a low cost of manufacture with regard to both materials and labor, and which accordingly is then susceptible of low prices of sale, thereby making such a gas delivery, evacuation and respiratory monitoring system and method economically available to the medical community.

Even still another object of the present invention is to provide a gas delivery, evacuation and respiratory monitoring system and method for allowing a user to deliver at least one gas and scavenge the exhausted gasses as well as monitor the exhausted gasses in a safe and efficient manner.

Lastly, it is an object of the present invention to provide a new and improved gas delivery, evacuation and respiratory monitoring system comprised of a face mask having an inflow flapper valve and a fresh-gas inflow tube and an exhaust-gas outflow tube and a gas sampling tube, a fresh gas source and an exhaust-gas scavenging system, a fresh gas supply tube operative coupling the fresh gas source and the face mask, an exhaust-gas hose operatively coupling the scavenging system and exhaust-gas outflow tube, a carbon-dioxide monitoring device, also known as a capnograph, and a carbon-dioxide sampling tube operative coupling the capnograph and the exhaust-gas sampling tube of the mask.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
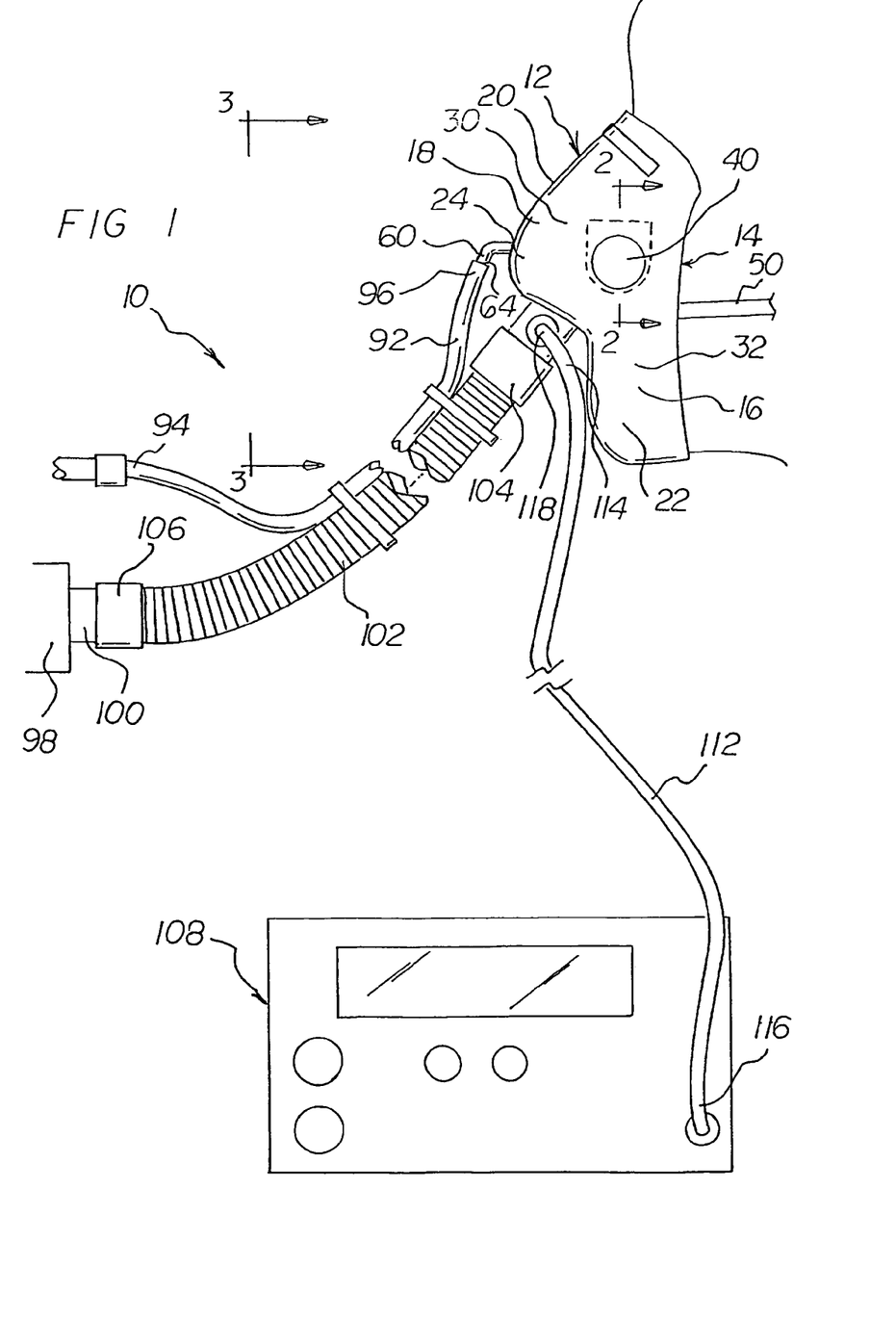
FIG. 1 is a side elevational view of a gas delivery, evacuation and respiratory monitoring system constructed in accordance with the principles of the present invention.

With reference now to the drawings, and in particular to FIG. 1 thereof, the preferred embodiment of the new and improved a gas delivery, evacuation and respiratory monitoring system and method embodying the principles and concepts of the present invention and generally designated by the reference numeral 10 will be described.

The present invention, a gas delivery, evacuation and respiratory monitoring system 10 and method is comprised of a plurality of components. Such components in their broadest context include a face mask, a fresh air source, an exhaust-gas scavenging system, an exhaust-gas hose, a carbon dioxide monitoring system and a carbon dioxide sampling tube. Such components are individually configured and correlated with respect to each other so as to attain the desired objective.

More specifically, a gas delivery, evacuation and respiratory monitoring system 10 is disclosed. The system allows a user to deliver at least one gas and scavenge the exhausted gasses. The system also allows a user to monitor the exhausted gases. The delivery, scavenging and monitoring can be done in a safe and efficient manner. The system comprises several components in combination. First provided is a face mask 12. The face mask is fabricated of a flexible material. The face mask has a face recipient area 14 and a continuous side wall area 16 and a dome area 18. The areas are continuous and form a surface.

Figure 3:
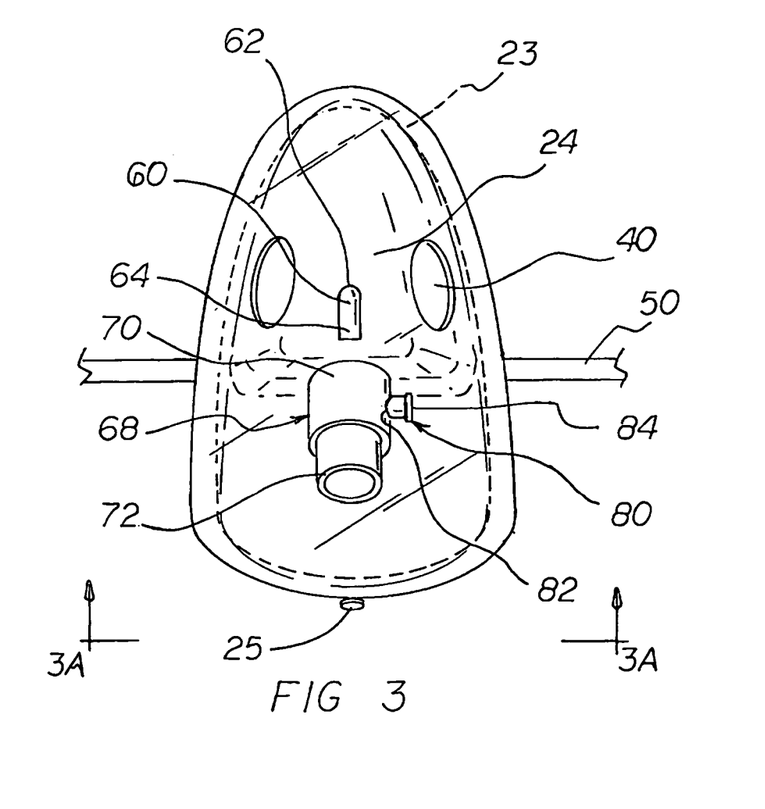
FIG. 3 is a front elevational view taken along line 3—3 of FIG. 1.
Figure 3A:
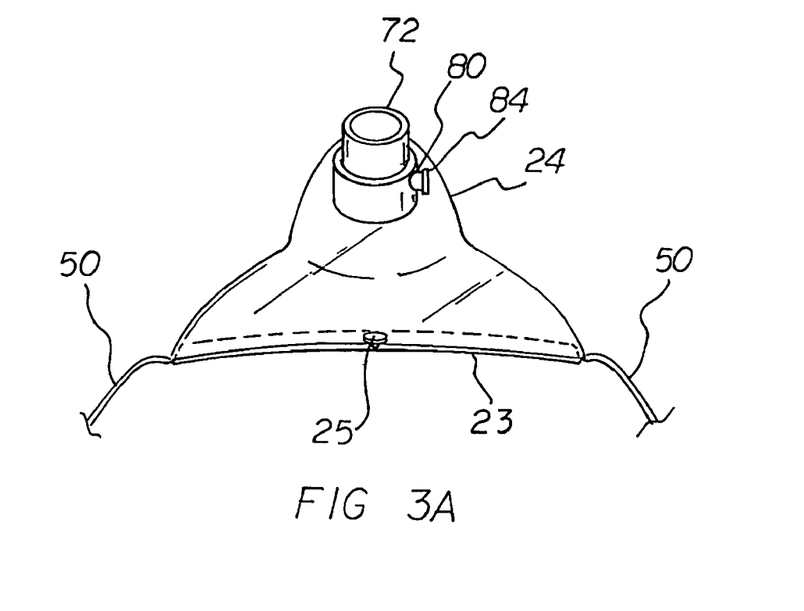
FIG. 3A is a bottom view taken along line 3A—3A of FIG. 3.

In an alternate embodiment, as shown in FIG. 3, the mask may have a soft cuff 23. The cuff may be made of a compressible material, or it may have an air space therein, the air being injected through a valve 25 that communicates with the space within the cuff.

Figure 6:
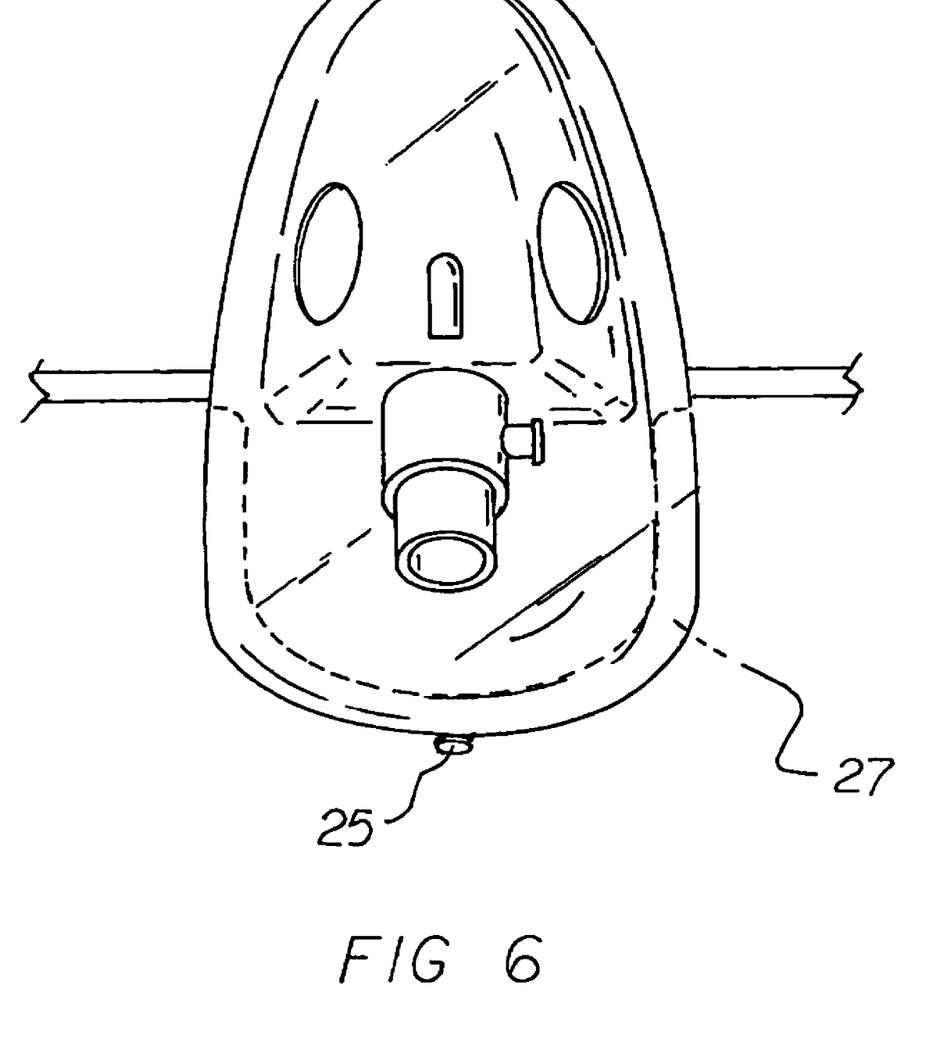
FIG. 6 is front elevation view of the face mask of the invention showing the partial cuff.

In an alternate embodiment a partial cuff 27 of the mask may only partially cover the edge. The cuff may be air inflated of the cuff may be fabricated of a soft compressible material, such as sponge rubber, as described above. While FIG. 6 depicts the partial cuff being located within the lower portion of the mask, it is understood that the partial cuff may be located on any portion of the mask, such as on the upper portion.

The mask has an upper portion 20 and a lower portion 22. The dome area is located in the upper portion of the mask. The dome forms a closed, recessed portion of the mask 24.

The face mask has a nasal portion 30 of a first width and a mouth portion 32 of a second width. The nasal and mouth portions are continuous, with the second width being larger than the first width.

The mask has a continuous side-wall with the side-wall having at least one intake hole 40 there through. The intake hole has an associated flapper valve 42, to permit the passage of a gas into the mask from the surrounding atmosphere and to prevent the gas from within the mask moving into the surrounding atmosphere.

Figure 2:
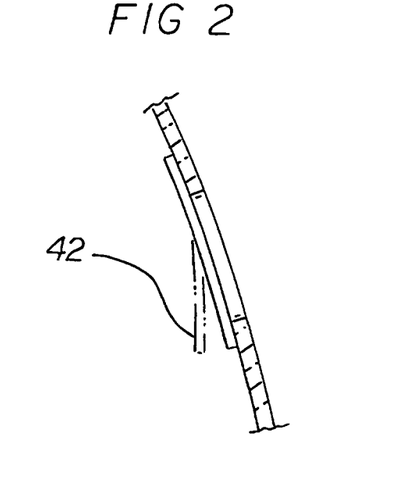
FIG. 2 is a cross sectional view taken along line 2—2 of FIG. 1.
Figure 2A:
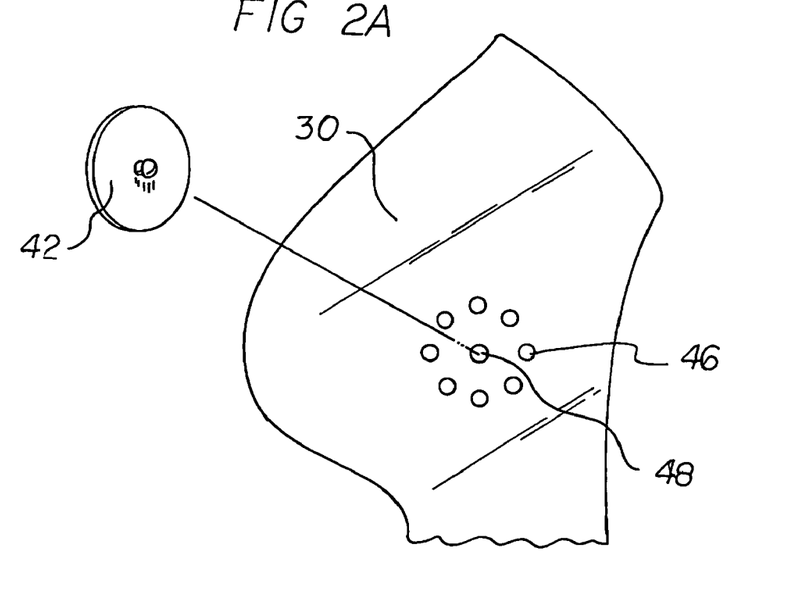
FIG. 2A is an exploded perspective view of the nasal portion, flapper valve and associated holes of the prior Figures.

In an alternate embodiment, as shown in FIG. 2A, the valve may be configured to have a plurality of radially located holes 46 located around a central hole 48. The valve is coupled with the central hole, and the radial holes allow the passage of gasses there through.

The mask has a head strap 50 that is coupled to the side wall of the mask to hold the mask in place. The head strap may be coupled to the mask by a slip fit means or by a snap means or a clip means.

The dome area has a fresh-gas inflow tube 60 of a first internal diameter coupled there to. The inflow tube has an inner portion 62 and an outer portion 64. The inner portion is coupled to the dome area of the face mask. The outer portion of the fresh-gas inflow tube has a tapered external second diameter to allow the slip-fit there onto.

The dome area also has an exhaust-gas outflow tube 68 of a third internal diameter and a fourth external diameter. The fourth diameter is larger than the first and second and third diameters. The exhaust-gas outflow tube has an inner portion 70 and an outer portion 72. The inner portion is coupled to the dome area of the face mask. The outer portion of the gas outflow tube is configured to allow the slip fit there onto.

The gas outflow tube also has an exhaust-gas sampling tube 80 of a fifth internal diameter coupled to the inner portion of the exhaust-gas outflow tube. The fifth diameter is smaller than the first, second, third and fourth diameters. The exhaust-gas sampling tube has an inward end 82 coupled to the exhaust-gas outflow tube and an outward end 84. The outward end has a male coupling thread 86.

Next provided is a fresh gas source 88 having a outflow tube 90.

Next provided is a fresh gas supply tube 92 fabricated of a flexible material. The gas supply tube has an inflow end 94 and an outflow end 96 having a second internal diameter. The inflow end is coupled to the outflow tube of the fresh gas source. The outflow end is coupled to the outer portion of the fresh-gas inflow tube of the face mask.

Next provided is an exhaust-gas scavenging system 98 having an inflow tube 100.

Next provided is an exhaust-gas hose 102. The exhaust-gas hose is fabricated of flexible material and has an inflow end 104 and an outflow end 106. The outflow end is coupled to the inflow tube of the exhaust-gas scavenging system. The inflow end has a fourth internal diameter so as to allow the exhaust-gas hose to be slipped onto and coupled with the outer portion of the exhaust-gas outflow tube.

Next provided is a carbon-dioxide monitoring device 108, also known as a capnograph. The device has a sample inflow tube 110 for receiving gas samples.

Lastly provided is a carbon-dioxide sampling tube 112 fabricated of a flexible material and having a fifth diameter. The carbon-dioxide sampling tube has an inflow end 114 and an outflow end 116. The outflow end is operatively coupled to the capnograph sample inflow tube. The inflow end of the carbon-dioxide sampling tube has a female treaded coupler 118 for receiving and coupling with the outward end of the exhaust-gas sampling tube of the mask.

Figure 4:
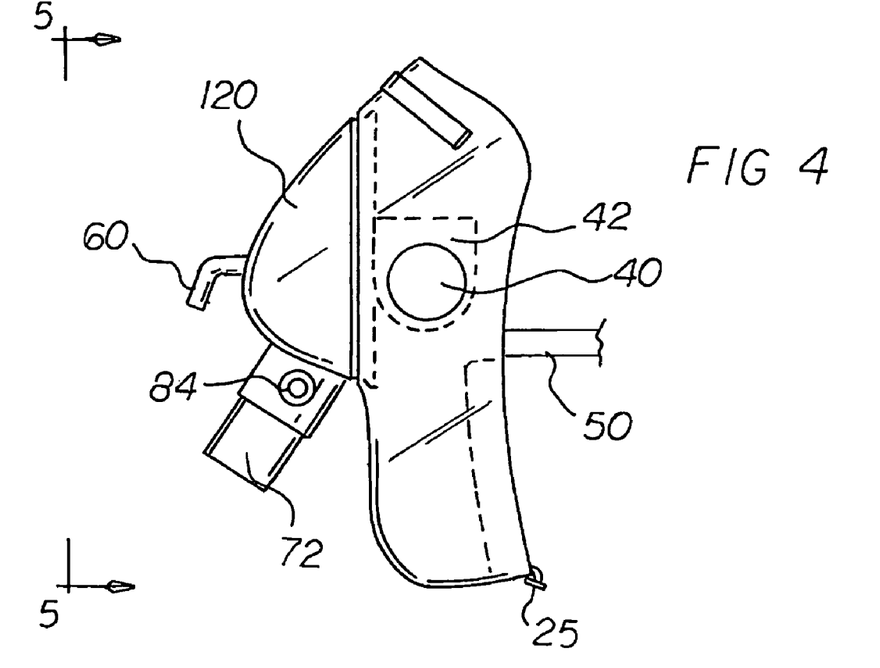
FIG. 4 is a side elevational view similar to FIG. 1 but illustrating an alternate embodiment of the invention.
Figure 5:
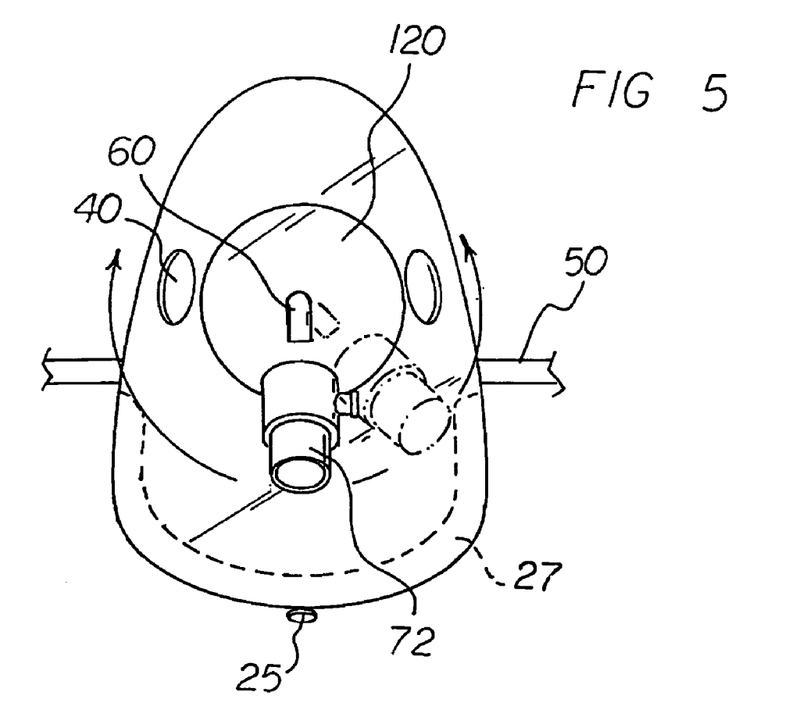
FIG. 5 is a front elevational view taken along line 5—5 of FIG. 4.

In an alternate embodiment, as shown in FIGS. 4 and 5, the dome of the mask may be a rotatable dome 120 and coupled to the mask nose portion so as to allow rotation of the dome in an azimuthal plane.

In addition to the system as described above, the present invention may also be considered as including a method for constructing a gas delivery, evacuation and respiratory monitoring system. Such method includes the steps of providing the components of the system as described above as well as the step of placing a system on a patient for allowing the system to deliver at least one gas and scavenge the exhausted gasses as well as monitor the exhausted gases in a safe and efficient manner. This allows a breath by breath analysis of carbon dioxide contents in the exhaled gasses, the system being configured to allow the safe administration of a gas to the face mask.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A gas delivery, evacuation and respiratory monitoring system for allowing a user to deliver at least one gas and scavenge the exhausted gasses as well as monitor the exhausted gases in a safe and efficient manner comprising, in combination:

a face mask fabricated of a flexible material and having a face recipient area and a continuous side wall area and a dome area forming a continuous surface, with the mask having an upper portion and a lower portion, the dome area being located in the upper portion of the mask with the dome forming a closed portion of the mask and forming a recess therein, the face mask having a nasal portion of a first width and a mouth portion of a second width, the nasal and mouth portions being continuous, with the second width being larger than the first width, the mask having a continuous side-wall portion with the side-wall portion having at least one intake hole there through with the intake hole having an associated flapper valve to permit the passage of a gas into the mask from the surrounding atmosphere and to prevent the gas from within the mask moving into the surrounding atmosphere, the mask having a head strap being coupled to the side wall of the mask to hold the mask in place, the dome area having a fresh-gas inflow tube of a first internal diameter coupled there to with the inflow tube having an inner portion and an outer portion, the inner portion being coupled to the dome area of the face mask, the outer portion of the fresh-gas inflow tube having a tapered external second diameter to allow the slip-fit there onto, the dome area also having an exhaust-gas outflow tube of a third internal diameter and a fourth external diameter with the fourth diameter being larger than the first and second and third diameters, the exhaust-gas outflow tube having an inner portion and an outer portion with the inner portion being coupled to the dome area of the face mask and the outer portion of the gas outflow tube configured to allow the slip fit there onto, the gas outflow tube also having an exhaust-gas sampling tube of a fifth internal diameter coupled to the inner portion of the exhaust-gas outflow tube, with the fifth diameter being smaller than the first, second, third and fourth diameters, the exhaust-gas sampling tube having an inward end coupled to the exhaust-gas outflow tube and an outward end, the outward end having a male coupling thread;

a fresh gas source having a outflow tube;

a fresh gas supply tube fabricated of a flexible material with the gas supply tube having an inflow end and an outflow end having a second internal diameter, the inflow end being coupled to the outflow tube of the fresh gas source and the outflow end being coupled to the outer portion of the fresh-gas inflow tube of the face mask;

an exhaust-gas scavenging system having an inflow tube;

an exhaust-gas hose, fabricated of flexible material and having an inflow end and an outflow end with the outflow end being coupled to the inflow tube of the exhaust-gas scavenging system, the inflow end having a fourth internal diameter so as to allow the exhaust-gas hose to be slipped onto and coupled with the outer portion of the exhaust-gas outflow tube;

a carbon-dioxide monitoring device, also known as a capnograph, the device having a sample inflow tube for receiving gas samples; and a carbon-dioxide sampling tube fabricated of a flexible material having a fifth diameter, the carbon-dioxide sampling tube having an inflow end and an outflow end, the outflow end being operatively coupled to the capnograph sample inflow tube and the inflow end of the carbon-dioxide sampling tube having a female treaded coupler for receiving and coupling with the outward end of the exhaust-gas sampling tube of the mask.

2. A gas delivery, evacuation and respiratory monitoring system comprising, in combination:

a face mask having an ambient-to-inside-the-mask inflow flapper valve with the flapper valve being located on the wall of the mask and a fresh-gas inflow tube and an exhaust-gas outflow tube and a gas sampling tube and a face recipient portion having a face recipient area with at least a part of the face recipient area of the mask being configured to have a seal so as to be in contact with a user's face;

a fresh gas source;

a fresh gas supply tube operative coupling the fresh gas source and the face mask;

an exhaust-gas scavenging system;

an exhaust-gas hose operatively coupling the scavenging system and exhaust-gas outflow tube;

a carbon-dioxide monitoring device, also known as a capnograph; and a carbon-dioxide sampling tube operatively coupling the capnograph and the exhaust-gas sampling tube of the mask.

3. A gas delivery, evacuation and respiratory monitoring system as described in claim 2 wherein the face mask further comprises:

a pair of face mask strap apertures and a face mask strap operatively coupled to the face mask strap apertures.

4. A gas delivery, evacuation and respiratory monitoring system as described in claim 2 wherein the face mask further comprises at least one inflow valve with the inflow valve comprising a plurality of radially located holes and a centrally located hole with the valve being coupled to the central hole so as to allow passage of gas through the radially placed holes, the gas moving in one direction.

5. A gas delivery, evacuation and respiratory monitoring system as described in claim 2 wherein face mask further comprises a dome portion, the dome portion being rotatably coupled with the face portion, the rotation of the dome allowing the fresh-gas inflow tube and exhaust-gas outflow tube to be directed in any azimuthal direction.

6. A method for constructing a gas delivery, evacuation and respiratory monitoring system comprising, in combination:

providing a face mask fabricated of a flexible material and having a face recipient portion with a face recipient area and a continuous side wall area and a dome area forming a continuous surface, with the mask having an upper portion and a lower portion, the dome area being located in the upper portion of the mask with the dome forming a closed portion of the mask and forming a recess therein, the face mask having a nasal portion of a first width and a mouth portion of a second width, the nasal and mouth portions being continuous, with the second width being larger than the first width, the mask having a continuous side-wall portion with the sidewall portion having at least one intake hole there through with the intake hole having an associated flapper valve to permit the passage of a gas into the mask from the surrounding atmosphere, the mask having a head strap being coupled to the side wall of the mask to hold the mask in place with at least a part of the face recipient area of the mask being configured to be in contact with a user's face, the dome area having a fresh-gas inflow tube of a first internal diameter coupled there to with the inflow tube having an inner portion and an outer portion, the inner portion being coupled to the dome area of the face mask, the outer portion of the fresh-gas inflow tube having a tapered external second diameter to allow the slip-fit there onto, the dome area also having an exhaust-gas outflow tube of a third internal diameter and a fourth external diameter with the fourth diameter being larger than the first and second and third diameters, the exhaust-gas outflow tube having an inner portion and an outer portion with the inner portion being coupled to the dome area of the face mask and the outer portion of the gas outflow tube configured to allow the slip fit there onto, the gas outflow tube also having an exhaust-gas sampling tube of a fifth internal diameter coupled to the inner portion of the exhaust-gas outflow tube, with the fifth diameter being smaller than the first, second, third and fourth diameters, the exhaust-gas sampling tube having an inward end coupled to the exhaust-gas outflow tube and an outward end, the outward end having a male coupling thread whereby the face mask can fit snugly against the face so as to minimize gas leakage;

providing a fresh gas source having a outflow tube whereby a gas may be provided to the system;

providing a fresh gas supply tube fabricated of a flexible material with the gas supply tube having an inflow end and an outflow end having a second internal diameter, the inflow end being coupled to the outflow tube of the fresh gas source and the outflow end being coupled to the outer portion of the fresh-gas inflow tube of the face mask whereby the fresh gas may be conducted to the face mask, thereby providing a source of fresh gas to the face area;

providing an exhaust-gas scavenging system having an inflow tube whereby a gas may be provided to the system thereby providing a means for the removal of exhausted gas;

providing an exhaust-gas hose, fabricated of flexible material and having an inflow end and an outflow end with the outflow end being coupled to the inflow tube of the exhaust-gas scavenging system, the inflow end having a fourth internal diameter so as to allow the exhaust-gas hose to be slipped onto and coupled with the outer portion of the exhaust-gas outflow tube whereby exhausted gasses are conducted away from the face mask, thereby allowing for the entry of fresh gas into the face mask;

providing a carbon-dioxide monitoring device, also known as a capnograph, the device having a sample inflow tube for receiving gas samples whereby a gas sample may be analyzed, thereby enabling a user to monitor and analyze a gas sample;

providing a carbon-dioxide sampling tube fabricated of a flexible material having a fifth diameter, the carbon-dioxide sampling tube having an inflow end and an outflow end, the outflow end being operatively coupled to the capnograph sample inflow tube and the inflow end of the carbon-dioxide sampling tube having a female treaded coupler for receiving and coupling with the outward end of the exhaust-gas sampling tube of the mask whereby a gas sample is conducted from the exhaust-gas tube to the capnograph for analysis, thereby allowing a breath by breath analysis of carbon dioxide contents in the exhaled gasses, the system being configured to allow the safe administration of a gas to the face mask; and placing a system on a patient for allowing the system to deliver at least one gas and scavenge the exhausted gasses as well as monitor the exhausted gases in a safe and efficient manner.

\* \* \* \* \*